(12) United States Patent
Farokhzad et al.

(10) Patent No.: US 7,550,441 B2
(45) Date of Patent: Jun. 23, 2009

(54) CONTROLLED RELEASE POLYMER NANOPARTICLE CONTAINING BOUND NUCLEIC ACID LIGAND FOR TARGETING

(75) Inventors: Omid C. Farokhzad, Boston, MA (US); Sangyong Jon, Gwangju (KR); Robert S. Langer, Newton, MA (US)

(73) Assignee: Massachusetts Institute of Technology, Boston, MA (US)

( * ) Notice: Subject to any disclaimer, the term of this patent is extended or adjusted under 35 U.S.C. 154(b) by 195 days.

(21) Appl. No.: 10/860,918

(22) Filed: Jun. 4, 2004

(65) Prior Publication Data
US 2005/0037075 A1   Feb. 17, 2005

Related U.S. Application Data

(63) Continuation-in-part of application No. 10/456,978, filed on Jun. 6, 2003.

(51) Int. Cl.
*A61K 31/7088* (2006.01)
*A61K 31/713* (2006.01)
*A61K 9/14* (2006.01)
*C12Q 1/00* (2006.01)
*C12N 11/00* (2006.01)

(52) U.S. Cl. ............................. 514/44; 514/2; 424/489; 435/4; 435/174

(58) Field of Classification Search ........................ None
See application file for complete search history.

(56) References Cited

U.S. PATENT DOCUMENTS

| | | | |
|---|---|---|---|
| 4,458,066 A | 7/1984 | Caruthers et al. | 536/27 |
| 5,459,015 A | 10/1995 | Janjic et al. | 435/6 |
| 5,731,144 A | 3/1998 | Toothman et al. | 435/6 |
| 5,766,853 A | 6/1998 | Parma et al. | 435/6 |
| 5,846,713 A | 12/1998 | Pagratis et al. | 435/6 |
| 5,869,641 A | 2/1999 | Jayasena et al. | 536/24.31 |
| 5,998,203 A | 12/1999 | Matulic-Adamic et al. | 435/325 |
| 6,004,534 A | 12/1999 | Langer et al. | 424/9.321 |
| 6,140,490 A | 10/2000 | Biesecker et al. | 536/24.31 |
| 6,207,649 B1 | 3/2001 | Weis et al. | 514/44 |
| 6,331,394 B1 | 12/2001 | Ruckman et al. | 435/6 |
| 6,379,699 B1 | 4/2002 | Virtanen et al. | 424/450 |
| 6,409,990 B1 | 6/2002 | Vera | 424/9.35 |
| 6,670,127 B2 | 12/2003 | Evans | 435/6 |
| 6,916,490 B1 | 7/2005 | Garver et al. | 424/489 |
| 7,029,897 B2 * | 4/2006 | Yue et al. | 435/196 |
| 7,312,325 B2 * | 12/2007 | Sullenger et al. | 536/24.5 |

FOREIGN PATENT DOCUMENTS

WO   WO 01/09156   2/2001

WO   WO 01/09157   2/2001

OTHER PUBLICATIONS

*Biesecker, et al., "Derivation of RNA Aptamer Inhibitors of Human Complement C5", *Immunopharmacology*, 42: 219-230, 1999.
*Bless, et al., "Protective Effects of an Aptamer Inhibitor of Neutrophil Elastase in Lung Inflammatory Injury", *Current Biology*, 7: 877-880, 1997.
*Blank, et al., "Systematic Evolution of a DNA Aptamer Binding to Rat Brain Tumor Microvessels", *The Journal of Biological Chemistry*, 276(19): 16464-16468, 2001.
*Bock, et al., "Selection of Single-Stranded DNA Molecules that Bind and Inhibit Human Thrombin", *Nature*, 355(6360):564-566, 1992.
*Bridonneau, et al., "High-Affinity Aptamers Selectively Inhibit Human Nonpancreatic Secretory Phospholipase A2 (hnps-PLA2)", *Journal of Medicinal Chemistry*, 41: 778-786, 1998.
*Davis, et al., "Staining of Cell Surface Human CD4 with 2'-F-Pyrimidine-Containing RNA Aptamers for Flow Cytometry", *Nucleic Acids Research*, 26: 3915-3924, 1998.
*Dougan, et al., "Extending the Lifetime of Anticoagulant Oligodeoxynucleotide Aptamers in Blood", *Nucl. Med. Bio*, 27(3): 289-297, 2000.
*Drolet, et al., Pharmacokinetics and Safety of an Anti-Vascular Endothelial Growth Factor Aptamer (NX1838) Following Injection into the Vitreous Humor of Rhesus Monkey's, *Pharmaceutical Research*, 17(12): 1503-1510, 2000.
*Eyetech Study Group, Preclinical and Phase 1A Clinical Evaluation of an Anti-VEGF Pegylated Aptamer (EYE001) for the Treatment of Exudative Age-Related Macular Degeneration, *Retina*, 22: 143-152, 2000.
*Famulok, et al., "Aptamers as Tools in Molecular Biology and Immunology", *Microbiol. Immunol.* 243: 123-136, 1999.
*Floege, et al., "Novel Approach to Specific Growth Factor Inhibition in Vivo: Antagonism of Platelet-Derived Growth Factor in Glomerulonephritis by Aptamers", *American Journal of Pathology*, 154: 169-179, 1999.
*Gold, et al., "From Oligonucleotide Shapes to Genomic SELEX: Novel Biological Regulatory Loops", *Proc. Natl. Acad. Sci. USA*, 94: 59-64, 1997.

(Continued)

*Primary Examiner*—David M Naff
(74) *Attorney, Agent, or Firm*—Lahive & Cockfield, LLP; Brian C. Trinque

(57) ABSTRACT

The present invention relates to a conjugate that includes a nucleic acid ligand bound to a controlled release polymer system, a pharmaceutical composition that contains the conjugate, and methods of treatment using the conjugate. The controlled release polymer system includes an agent such as a therapeutic, diagnostic, prognostic, or prophylactic agent. The nucleic acid ligand that is bound to the controlled release polymer system, binds selectively to a target, such as a cell surface antigen, and thereby delivers the controlled release polymer system to the target.

37 Claims, 4 Drawing Sheets

OTHER PUBLICATIONS

*Green, et al., "Nuclease-Resistant Nucleic Acid Ligands to Vascular Permeability Factor/Vascular Edothelial Growth Factor", *Chem Biol.*, 2(10): 683-695, 1995.
*Green, et al., "Inhibitory DNA Ligands to Platelet-Derived Growth Factor B-Chain", *Biochemistry*, 35: 14413-14424, 1996.
*Griffin, et al., "In Vivo Anticoagulant Properties of a Novel Nucleotide-Based Thrombin Inhibitor and Demonstration of Regional Anticoagulation in Extracorporeal Circuits", *Blood*, 81(12): 3271-3276, 1993.
*Hicke, et al., "Escort Aptamers: A Delivery Service for Diagnosis and Therapy", *The Journal of Clinical Investigation*, 106(8): 923-928, 2000.
*Hicke, et al., "DNA Aptamers Block L-Selectin Function in Vivo, Inhibition of Human Lymphocyte Trafficking in SCID Mice", *Journal of Clinical Investigation*, 98: 2688-2692, 1996.
*Jayasena, S., "Aptamers: An Emerging Class of Molecules That Rival Antibodies in Diagnostics", *Clinical Chemistry*, 45(9): 1628-1650, 1999.
*Jellinek, et al., "Inhibition of Receptor Binding by High Affinity RNA Ligands to Vascular Endothelial Growth Factor", *Biochemistry*, 33: 10450-10456, 1994.
*Jellinek, et al., "Potent 2'-Amino-2'- Deoxypyrimidine RNA Inhibitors of Basic Fibroblast Growth Factor", *Biochemistry*, 36:11363-11372, 1995.
*Jellinek, et al., "High Affinity RNA Ligands to Basic Fibroblast Growth Factor Inhibit Receptor Binding", *Proc. Natl. Acad. Sci. USA*, 90: 11227-11231, 1993.
*Jenison, et al., "Oligonucleotide Inhibitors of P-Selectin-Dependent Neutrophil-Platelet Adhesion", *Antisense Nucleic Acid Drug Dev.*, 4: 265-279, 1998.
*Kopylov, et al., "Combinatorial Chemistry of Nucleic Acids: SELEX", *Molecular Biology*, 34(6): 940-954, 2000.
*Kubik, et al., "Isolation and Characterization of 2'-Fluoro-2'-amino-, and 2'-Fluoro-/Amino-Modified RNA Ligands to Human IFN-Gamma That Inhibit Receptor Binding", *J. Immunology*, 159: 259-267, 1997.
*Kubik, et al., "High-Affinity RNA Ligands to Human Alpha-Thrombin", *Nucleic Acids Research*, 22: 2619-2626, 1994.
*Lee, et al., "A Novel Oligodeoxynucleotide Inhibitor of Thrombin. II. Pharmacokinetics in the Cynomolgus Monkey", *Pharm. Res.* 12(12): 1943-1947, 1995.
*Leppanen, et al., "Intimal Hyperplasia Recurs After Removal of PDGF-AB and -BB Inhibition in the Rat Carotid Artery Injury Model", *Aterioscler, Thromb. Vasc. Biol.*, 20: E89-95, 2000.
*Li, et al., "A Novel Nucleotide-Based Thrombin Inhibitor Inhibits Clot-Bound Thrombin and Reduces Arterial Platelet Thrombus Formation", *Blood*, 83(3): 677-682, 1994.
*Lupold, et al., "Identification and Characterization of Nuclease-Stabilized RNA Molecules that Bind Human Prostate Cancer Cels via the Prostate-Specific Membrane Antigen", *Cancer Research*, 62: 4029-4033, 2002.
*Meyer, et al., "Targeting a Genetically Engineered Elastin-Like Polypeptide to Solid Tumors by Local Hyperthermia", *Cancer Research*, 61: 1548-1554, 2001.

*O'Connell, et al., "Calcium-Dependent Oligonucleotide Antagonists Specific for L-Selectin", *Proc. Natl. Acad. Sci. USA*, 93: 5883-5887, 1996.
*Osborne, et al., "Aptamers as Therapeutic and Diagnostic Reagents: Problems and Prospects", *Curr. Opin. Chem. Biol.* 1:5-9, 1997.
*Ostendorf, et al., "The Effects of PDGF Antagonism in Experimental Glomerulonephritis are Independent of the TGF-Beta System", *J. Amer. Soc. Nephrology*, 13: 658-667, 2002.
*Ostendorf, et al., "VEGF165 Mediates Glomerular Endothelial Repair", *J. Clinical Invest.* 104: 913-923, 1999.
*Ostendorf, et al., "Specific Antagonism of PDGF Prevents Renal Scarring in Experimental Glomerulonephritus", *J. Amer. Soc. Nephrology*, 12: 909-918, 2001.
*Pagratis, et al., "Potent 2'-Amino-, and 2'-Fluoro-2'-Deoxyribonucleotide RNA Inhibitors of Keratinocyte Growth Factor", *Nature Biotechnology*, 15: 68-73, 1997.
*Patel, et al., "Structure, Recognition and Discrimination in RNA Aptamer Complexes with Cofactors, Amino Acids, Drugs and Aminoglycoside Antibiotics", *Reviews in Molecular Biotechnology*, 74: 39-60, 2000.
*Pieken, et al., "Kinetic Characterization of Ribonuclease-Resistant 2'-Modified Hammerhead Ribozymes", *Science*, 253(5017): 314-317, 1991.
*Pietras, et al., "Inhibition of Platelet-Derived Growth Factor Receptors Reduces Interstitial Hypertension and Increases Transcapillary Transport in Tumors", *Cancer Research*, 61: 2929-2934, 2001.
*Reyderman, et al., "Pharmacokinetics and Biodistribution of a Nucleotide-Based Thrombin Inhibitor in Rats", *Pharm Res.* 15(6): 904-910, 1998.
*Ringquist, et al., "Anti-L-Selectin Oligonucleotide Ligands Recognize CD26L-Postive CD26L-Postive Leukocytes: Binding Affinity and Specificity of Univalent and Bivalent Ligands", *Cytometry*, 33: 394-405, 1998.
*Ruckman, et al., "2'Fluoropyrimidine RNA-Based Aptamers to the 165-Amino Acid Form of VEGF", *J. Biological Chem.*, 273: 20556-20567, 1998.
*Sullenger, B., "Emerging Clinical Applications of Nucleic Acids", *The Journal of Clinical Investigation*, 106(8): 921-922, 2000.
*Tasset, et al., "Oligonucleotide Inhibitors of Human Thrombin that Bind Distinct Epitopes", *Journal of Molecular Biology*, 272: 688-698, 1997.
*Tucker, et al., "Detection and Plasma Pharmacokinetics of an Anti-Vascular Endothelial Growth Factor Oligonucleotide-Aptamer (NX1838) In Rhesus Monkeys", *Journal of Chromatography B*, 732: 203-212, 1999.
*Watson, et al., "Anti-L-Selectin Aptamers: Binding Characteristics, Pharmacokinetic Parameters, and Activity Against an Intravascular Target in Vivo", *Antisense Nucleic Acid Drug Development*, 2:63-75, 2000.
*White, et al., "Developing Aptamers into Therapeutics", *The Journal of Clinical Investigation*, 106(8): 929-934, 2000.
*Wiegand, et al., "High-Affinity Oligonucleotide Ligands to Human IgE Inhibit Binding to Fc Epsilon Receptor I", *Journal of Immunology*, 157: 221-230, 1996.
*Willis, et al., "Liposome-Anchored Vascular Endothelial Growth Factor Aptamers", *Bioconjugate Chem.* 9: 573-582,1998.

* cited by examiner

Figure 4A-D

CONTROLLED RELEASE POLYMER NANOPARTICLE CONTAINING BOUND NUCLEIC ACID LIGAND FOR TARGETING

RELATED APPLICATIONS

This application is a Continuation-in-Part of U.S. application Ser. No. 10/456,978, filed Jun. 6, 2003, the entire teachings of which are incorporated herein by reference.

This invention was made with government support under Grant Number EEC-9843342, awarded by The National Science Foundation ("NSF"). The government has certain rights in the invention.

BACKGROUND

The delivery of a drug to a patient with controlled-release of the active ingredient has been an active area of research for decades and has been fueled by the many recent developments in polymer science and the need to deliver more labile pharmaceutical agents such as nucleic acids, proteins, and peptides. In addition, controlled release polymer systems can be designed to provide a drug level in the optimum range over a longer period of time than other drug delivery methods, thus increasing the efficacy of the drug and minimizing problems with patient compliance.

Biodegradable particles have been developed as sustained release vehicles used in the administration of small molecule drugs as well as protein and peptide drugs and nucleic acids (Langer, *Science*, 249:1527-1533, 1990; Mulligan, *Science*, 260:926-932,1993; Eldridge, *Mol. Immunol.*, 28:287-294, 1991, the entire teaching of each of the foregoing references are incorporated herein by reference). The drugs are typically encapsulated in a polymer matrix which is biodegradable and biocompatible. As the polymer is degraded and/or as the drug diffuses out of the polymer, the drug is released into the body. Typically, polymers used in preparing these particles are polyesters such as poly(glycolide-co-lactide) (PLGA), polyglycolic acid, poly-β-hydroxybutyrate, and polyacrylic acid ester. These particles have the additional advantage of protecting the drug from degradation by the body. Furthermore, these particles depending on their size, composition, and the drug being delivered can be administered to an individual using any route available.

Targeting controlled release polymer systems (e.g., targeted to a particular tissue or cell type or targeted to a specific diseased tissue but not normal tissue) is desirable because it reduces the amount of a drug present in tissues of the body that are not targeted. This is particularly important when treating a condition such as cancer where it is desirable that a cytotoxic dose of the drug is delivered to cancer cells without killing the surrounding non-cancerous tissue. Effective drug targeting should reduce the undesirable and sometimes life threatening side effects common in anticancer therapy.

With advances in immunology and molecular biology, it is now possible to target specific tissues or cells directly by using antibodies or antibody fragments to antigens unique to or more prevalent in the target tissue or cell. Antibodies have been used for immunotherapy directly or as vehicles to deliver drugs to tissues or cells. However, this approach was first attempted using monoclonal antibodies to deliver chemotherapeutic agents in the 1980's and proved to be considerably more difficult than anticipated. Several obstacles including immunotoxicity, poor tumor/plasma distribution and poor tumor penetration by the antibodies. Immunotoxicity has been mitigated by using humanized and engineered monoclonal antibodies. However, poor tumor/plasma distribution and poor tumor penetration by the antibodies has been attributed to the large size of monoclonal antibodies and remains an important consideration today. Despite recent success of monoclonal antibodies as drugs, this class of molecule continues to exhibit suboptimal properties as vehicles for drug delivery, largely because of their large size.

Moreover, the biological production of monoclonal antibodies can be difficult and unpredictable. Antibody generation can be difficult if the target antigen is not well tolerated by the animal used to produce the antibodies (e.g., toxins). Furthermore, some target molecules are inherently less immunogenic making it difficult to raise antibodies against such targets. In addition, the performance of antibodies can vary from batch to batch, in particular when production is scaled-up.

It would be desirable to develop drug targeting vehicles that that can be used to target the delivery of controlled release polymer systems like monoclonal antibodies with high specificity but which overcome or ameliorate some of the problems associated with the use and production of monoclonal antibodies.

SUMMARY OF THE INVENTION

The present invention relates to a conjugate that includes a nucleic acid ligand bound to a controlled release polymer system, a pharmaceutical composition that contains the conjugate, and methods of treatment using the conjugate. The controlled release polymer system includes an agent such as a therapeutic, diagnostic, prognostic, or prophylactic agent. The nucleic acid ligand that is bound to the controlled release polymer system, binds selectively to a target, such as a cell surface antigen, and thereby delivers the controlled release polymer system to the target. The conjugate of the invention can be used to deliver an agent to a target cell by contacting the target cell with the conjugate.

Particular developmental stages of tissues are typically marked by specific cell surface antigens or express particular cell surface antigens significantly more frequently than tissues in another developmental stage. In one embodiment, the conjugate binds to a cell surface antigen specific to or more frequently expressed in a tissue in a specific developmental stage.

Particular disease states of a tissue, such as cancer, are typically marked by specific cell surface antigens or express a particular cell surface antigen more frequently than normal tissue. In one embodiment, the conjugate binds to a cell surface antigen specific to or more frequently expressed in a diseased state of a tissue.

In anther embodiment, a conjugate of the invention can be used to treat, diagnose or predict the outcome of a patient with cancer. The method involves administering to the patient a conjugate that comprises a nucleic acid ligand bound to a controlled release polymer system, wherein the nucleic acid ligand selectively binds to tumor cells.

The nucleic acid ligands are DNA or RNA oligonucleotides or modified DNA or RNA oligonucleotides that fold by intramolecular interactions into unique conformations. Like antibodies, nucleic acid ligands can be prepared that bind to target antigens with high specificity and affinity and thus can be used as targeting vehicles. However, the use of nucleic acid ligands as targeting vehicles has several advantages over antibodies. For example, nucleic acid ligands with a high affinity for a target can be prepared through a chemical process called Systemic Evolution of Ligands by Exponential Enrichment (SELEX), or a variation thereof. Nucleic acid ligands isolated using the SELEX process are relatively small as compared to antibodies, lack immunogenicity, and have been shown to have better tumor/plasma distribution, and are expected to have better tumor penetration potential. Moreover, since the SELEX process is a completely chemical process that does not involve animals, nucleic acid ligands can be prepared that bind to any target regardless of the toxicity or immunogenicity of the target. Furthermore, a nucleic acid ligand identified through the SELEX process can be synthesized using chemical oligonucleotide synthesis which has been shown to scale-up well so nucleic acid ligands can be prepared with little or no variation from batch to batch in binding affinity.

DESCRIPTION OF THE FIGURES

This patent or application file contains at least one drawing executed in color. Copies of this patent or patent application publication with color drawings will be provided by the Office upon request and payment of the necessary fee.

FIG. 4A is a light microscopy image of PLA-PEG-COOH microparticles that have been incubated with a 5'-FITC labeled amine-modified aptamers in the absence of EDC.

FIG. 4B is a fluorescent image of the microparticles in FIG. 4A.

FIG. 4C is a light microscopy image of PLA-PEG-COOH microparticles that have been incubated with a 5'-FITC labeled amine-modified aptamer in the presence of EDC.

FIG. 4D is a fluorescent image of the microparticles in FIG. 4C.

DETAILED DESCRIPTION OF THE INVENTION

Figure 1:
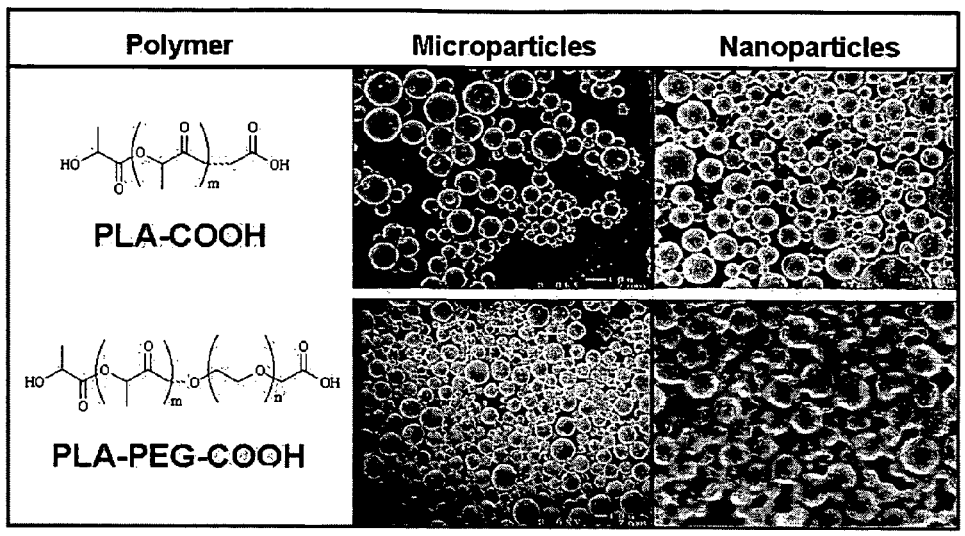
FIG. 1 is an SEM image of mico- and nanoparticles generated from poly (lactic acid) polymer with a terminal carboxylic acid group (PLA-COOH) and mico- and nanoparticles generated from poly (ethylene glycol)-poly (lactic acid) en-block co-polymer with a terminal carboxylic acid group (PLA-PEG-COOH).

A novel class of compounds known as nucleic acid ligands, for example aptamers, have recently been developed which rival antibodies in their potential for therapeutic and diagnostic use in many areas of medicine including oncology. Nucleic acid ligands are DNA or RNA oligonucleotides or modified DNA or RNA oligonucleotides that fold by intramolecular interactions into unique conformations capable of binding to target antigens with high specificity and affinity. Nucleic acid ligands for any antigen can be isolated by the Systemic Evolution of Ligands by Exponential Enrichment (SELEX), a technique first described by Tuerk and Gold in 1990 (Tuerk and Gold, *Science*(1990), 249:505-510, the entire teachings of which are incorporated herein by reference). Since their original description, nucleic acid ligands have been generated to a wide variety of targets, including intracellular proteins, transmembrane proteins, such as CD40 (U.S. Pat. No. 6,171,795, the entire teachings of which are incorporated herein by reference), soluble proteins, such as immunoglobulin E (U.S. Pat. Nos. 5,686,592 and 5,629,155, the entire teachings of both patents are incorporated herein by reference) and small molecule drugs, such as caffeine and theophylline (U.S. Pat. No. 5,580,737, the entire teachings of which are incorporated herein by reference). To date more than 100 nucleic acid ligands have been isolated, and one nucleic acid ligand against the Vascular Endothelial Growth Factor (VEGF)165 protein is currently in Phase III clinical trials for the treatment of neovascular macular degeneration (U.S. Pat. Nos. 6,426,335, 6,168,778, 6,051,698, 5,859,228, 5,849,479 and 5,811,533, all of which are incorporated herein by reference in their entirety). However, despite their similarity to antibodies in binding selectivity, nucleic acid ligands have not yet been fully exploited as delivery vehicles for therapeutic, diagnostic, prognostic and prophylactic agents. In particular, a conjugate of a nucleic acid ligand and a controlled release polymer system has not yet been demonstrated.

The present invention relates to a conjugate that has a nucleic acid ligand bound to a controlled release polymer system. A controlled release polymer system, as used herein, is a polymer combined with an active agent, such as a therapeutic agent, a diagnostic agent, a prognostic, or prophylactic agent, so that the active agent is released from the material in a predesigned manner. For example, the active agent may be released in a constant manner over a predetermined period of time, it may be released in a cyclic manner over a predetermined period of time, or an environmental condition or external event may trigger the release of the active agent. The controlled release polymer system may include a polymer that is biologically degradable, chemically degradable, or both biologically and chemically degradable.

Examples of suitable polymers for controlled release polymer systems include, but are not limited to, poly(lactic acid), derivatives of poly(lactic acid), PEGylated poly(lactic acid), poly(lactic-co-glycolic acid), derivatives of poly(lactic-co-glycolic acid), PEGylated poly(lactic-co-glycolic acid), polyanhydrides, poly(ortho esters) derivatives of pholy(ortho esters), PEGylated poly(ortho esters), poly(caprolactones), derivatives of poly(caprolactone), PEGylated poly(caprolactone), polylysine, derivatives of polylysine, PEGylated polylysine, poly(ethylene imine), derivatives of poly(ethylene imine), PEGylated poly(ethylene imine), poly(acrylic acid), derivatives of poly(acrylic acid), poly(urethane), derivatives of poly(urethane), and combinations thereof. In a preferred embodiment, the controlled release polymer system is a microsphere or a nanosphere.

As used herein, "degradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In preferred embodiments, the degradable polymers and their degradation byproducts are biocompatible.

The term "biocompatible" polymer, as used herein is intended to describe polymers that are not toxic to cells. Compounds are "biocompatible" if their addition to cells in vitro results in less than or equal to 20% cell death and if they do not induce significant inflammation or other such significant adverse effects in vivo.

Biocompatible polymers can be categorized as biodegradable and non-biodegradable. Biodegradable polymers degrade in vivo as a function of chemical composition, method of manufacture, and implant structure. Synthetic and natural polymers can be used although synthetic polymers are preferred due to more uniform and reproducible degradation and other physical properties. Examples of synthetic polymers include polyanhydrides, polyhydroxyacids such as polylactic acid, polyglycolic acids and copolymers thereof, polyesters, polyamides, polyorthoesters, and some polyphosphazenes. Examples of naturally occurring polymers include proteins and polysaccharides such as collagen, hyaluronic acid, albumin and gelatin. Drug can be encapsulated within, throughout, and/or on the surface of the implant. Drug is released by diffusion, degradation of the polymer, or a combination thereof. There are two general classes of biodegradable polymers: those degrading by bulk erosion and those degrading by surface erosion. U.S. Patents that describe the use of polyanhydrides for controlled delivery of substances include U.S. Pat. No. 4,857,311 to Domb and Langer, U.S. Pat. No. 4,888,176 to Langer, et al., and U.S. Pat. No. 4,789,724 to Domb and Langer.

Other polymers such as polylactic acid, polyglycolic acid, and copolymers thereof have been commercially available as suture materials for a number of years and can be readily formed into devices for drug delivery.

Non-biodegradable polymers remain intact in vivo for extended periods of time (e.g., at least about one or more years). Drug loaded into the non-biodegradable polymer matrix is released by diffusion through the polymer's micropore lattice in a sustained and predictable fashion, which can be tailored to provide a rapid or a slower release rate by altering the percent drug loading, porosity of the matrix, and implant structure. Ethylene-vinyl acetate copolymer (EVAc) is an example of a nonbiodegradable polymer that has been used as a local delivery system for proteins and other micromolecules, as reported by Langer, R., and J. Folkman, Nature (London) 263:797-799 (1976). Others include polyurethanes, polyacrylonitriles, and some polyphosphazenes.

Cationic polymers have been widely used as transfection vectors due to the facility with which they condense and protect negatively charged strands of DNA. Amine-containing polymers such as poly(lysine) (Zauner et al., *Adv. Drug Del Rev.*, 30:97-113, 1998; Kabanov et al., *Bioconjugate Chem.*, 6:7-20,1995, the entire teachings of each of the foregoing references are incorporated herein by reference), poly (ethylene imine) (PEI) (Boussif et al., *Proc. Natl. Acad. Sci. USA*, 92:7297-7301,1995, the entire teachings of which are incorporated herein by reference), and poly(amidoamine) dendrimers (Kukowska-Latallo et al., *Proc. Natl. Acad. Sci. USA*, 93:48974902, 1996; Tang et al., *Bioconjugate Chem.* 7:703-714, 1996; Haensler et al., *Bioconjugate Chem.*, 4:372-379,1993; the entire teachings of each of the foregoing references are incorporated herein by reference) are positively-charged at physiological pH, form ion pairs with nucleic acids, and mediate transfection in a variety of cell lines.

Degradable polyesters bearing cationic side chains have also been developed (Putnam et al., *Macromolecules*, 32:3658-3662, 1999; Barrera et al., *J. Am. Chem. Soc.*, 115: 11010-11011,1993; Kwon et al., *Macromolecules*, 22:3250-3255,1989; Lim et al., *J. Am. Chem. Soc.*, 121:5633-5639, 1999; Zhou et al., *Macromolecules*, 23:3399-3406,1990, the entire teachings of each of the foregoing references are incorporated herein by reference). Examples of these polyesters include poly(L-lactide-co-L-lysine) (Barrera et al., *J. Am. Chem. Soc.*, 115:11010-11011,1993; the entire teachings of which are incorporated herein by reference), poly(serine ester) (Zhou et al., *Macromolecules*, 23:3399-3406, 1990, the entire teaching of each of the foregoing references are incorporated herein by reference), poly(4-hydroxy-L-proline ester) (Putnam et al., *Macromolecules*, 32:3658-3662,1999.; Lim et al., *J. Am. Chem. Soc.*, 121:5633-5639,1999, the entire teachings of each of the foregoing references are incorporated herein by reference). Poly(4-hydroxy-L-proline ester) was recently demonstrated to condense plasmid DNA through electrostatic interactions, and to mediate gene transfer (Putnam et al., *Macromolecules*, 32:3658-3662,1999; Lim et al., *J. Am. Chem. Soc.*, 121:5633-5639,1999, the entire teachings of each of the foregoing references are incorporated herein by reference). Importantly, these new polymers are significantly less toxic than poly(lysine) and PEI, and they degrade into non-toxic metabolites.

The term "nucleic acids," or "oligonucleotides," as used herein, refers to a polymer of nucleotides. Typically, a nucleic acid comprises at least three nucleotides. The polymer may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available (e.g. see, www.trilinkbiotech.com, www.appliedbiosystems.com, www.biogenex-.com or www.syngendna.com).

As used herein, "nucleic acid ligand" is a non-naturally occurring nucleic acid that binds selectively to a target. The nucleic acid that forms the nucleic acid ligand may be composed of naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In one embodiment, nucleotides or modified nucleotides of the nucleic acid ligand can be replaced with a hydrocarbon linker or a polyether linker provided that the binding affinity and selectivity of the nucleic acid ligand is not substantially reduced by the substitution (e.g., the dissociation constant of the nucleic acid ligand for the target should not be greater than about $1 \times 10^{-6}$ M). The target molecule of a nucleic acid ligand is a three dimensional chemical structure that binds to the nucleic acid ligand. However, the nucleic acid ligand is not simply a linear complementary sequence of a nucleic acid target but may include regions that bind via complementary Watson-Crick base pairing interrupted by other structures such as hairpin loops). In the present invention, the targets include peptide, polypeptide, carbohydrate and nucleic acid molecules. In one embodiment, the nucleic acid ligand binds to a cell or tissue in a specific developmental stage or a specific disease state. A preferred target is an antigen on the surface of a cell, such as a cell surface receptor, an integrin, a transmembrane protein, and ion channel or a membrane transport protein. More preferably, the target is a tumor-marker. A tumor-marker is an antigen that is present in a tumor that is not present in normal tissue or an antigen that is more prevalent in a tumor than in normal tissue.

Nucleic acid ligands may be prepared by any method. However, a preferred method of preparing nucleic acid ligands is to identify nucleic acid ligands from a candidate mixture of nucleic acids. Systemic Evolution of Ligands by Exponential Enrichment (SELEX), or a variation thereof, is a commonly used method of identifying nucleic acid ligands that bind to a target from a candidate mixture of nucleic acids.

The SELEX process for obtaining nucleic acid ligands is described in U.S. Pat. No. 5,567,588, the entire teachings of which are incorporated herein by reference. Briefly, the basic SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the potential of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with a selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 0.1%-10%) is retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a small number of unique nucleic acids representing those nucleic acids from the original candidate mixture having the highest affinity to the target molecule. Preferably, the nucleic acid ligands identified will have a dissociation constant with the target of about $1 \times 10^{-6}$ M or less. Typically, the dissociation constant of the nucleic acid ligand and the target will be in the range of between about $1 \times 10^{-8}$ M and about $1 \times 10^{-12}$ M.

Nucleic acid ligands that bind selectively to any antigen can be isolated by the SELEX process, or a variation thereof, provided that the antigen can be used as a target in the SELEX process. For example, nucleic acid ligands that bind to a protein, a carbohydrate or a nucleic acid can be prepared. In one embodiment, nucleic acid ligands can be prepared and used in the conjugates of the invention that bind to proteins, such as tumor-markers, integrins, cell surface receptors, transmembrane proteins, intercellular proteins, ion channels, membrane transporter protein, enzymes, antibodies, and chimeric proteins. In another embodiment, nucleic acid ligands can be prepared and used in the conjugates of the invention that bind to carbohydrate, such as glycoproteins, sugar residues (e.g., monosaccharides, disaccharides and polysaccharides) and glycocalyx (i.e., the carbohydrate-rich peripheral zone on the outside surface of most eucaryotic cells). In another embodiment, nucleic acid ligands can be prepared and used in the conjugates of the invention that bind to a nucleic acid, such as DNA nucleic acids, RNA nucleic acids, modified DNA nucleic acids, modified RNA nucleic acids or nucleic acids that include any combination of DNA, RNA, modified DNA, and modified RNA. In a preferred embodiment, the nucleic acid ligand used in the conjugates of the invention binds to a cell surface antigen.

Preferably, the nucleic acid ligand is resistant to endonuclease and exonuclease degradation. Typically, nucleic acid ligands that includes one or more modified nucleotide exhibit improved resistant to endo- and exonuclease degradation. A particularly preferred nucleic acid ligand is a spiegelmer which is composed of L-enantiomeric nucleotides and is resistant to endo- and exonucleases. The nucleic acid ligands used in the conjugates of the invention can also include one or more internal nucleotides at the 3'-end, 5'-end, or at both the 3'- and 5'-end that is inverted to yield a 3'-3' or a 5'-5' nucleotide linkage.

Nucleic acid ligands can increase the specificity of the controlled release polymer system that contains a therapeutic, diagnostic and prognostic agents, thus increasing their efficacy while decreasing their toxicity. For example, in a conjugate designed for a therapeutic application, a nucleic acid ligand can be conjugated with a controlled release polymer system that includes a toxin, radionuclide or chemotherapeutic drug; this conjugated nucleic acid ligand may be simplistically viewed as a guided missile with the nucleic acid ligand as the guidance system and the drug as the warhead. In addition, nucleic acid ligand conjugated with radionuclides or metallic tracers can be used for proton emission (PET) and nuclear magnetic resonance (NMR) imaging for in vivo diagnosis and determination of the location of, for example, metastases.

The conjugate of the invention can also include an agent for localization that aids in positioning the conjugate in the vicinity of the target cell or tissue. For example, a magnetic particle may be attached to the conjugate as a localizing agent. The conjugate can then be administered to the patient intravenous, for example, and external magnets can be positioned so that a magnetic field is created within the body at the site of the target tissue. The magnetic particle that is attached to the conjugate is then drawn to the magnetic field and retained there until the magnet is removed. In one embodiment, the magnetic particle includes elemental iron.

The agents to be incorporated in the controlled release polymer system and delivered to a target cell or tissue by a conjugate of the present invention may be therapeutic, diagnostic, prophylactic or prognostic agents. Any chemical compound to be administered to an individual may be delivered using the conjugates of the invention. The agent may be a small molecule, organometallic compound, nucleic acid, protein, peptide, polynucleotide, metal, an isotopically labeled chemical compound, drug, vaccine, immunological agent, etc.

In a preferred embodiment, the agents are organic compounds with pharmaceutical activity. In another embodiment of the invention, the agent is a small molecule that is a clinically used drug. In a particularly preferred embodiment, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, adrenergic blocking agent, diuretic, cardiovascular active agent, vasoactive agent, non-steroidal anti-inflammatory agent, nutritional agent, etc.

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 2500 g/mol. Also, small molecules typically have multiple carbon-carbon bonds. Small molecules include, but are not limited to, an antibiotic, an antiviral, an antiparasitic agent, an anti-cancer agent, a radionuclide, an anticoagulant, an analgesic agent, an anesthetic agent, an ion channel potentiator, an ion channel inhibitor, an anti-inflammatory and combinations thereof. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

In another embodiment, the agent is a protein drug, such as an antibody, an antibody fragment, a recombinant antibody, a recombinant protein, a purified protein, a peptide, an amino acid and combinations thereof. According to the present invention, a "peptide" or "protein" comprises a string of at least three amino acids linked together by peptide bonds. The terms "protein" and "peptide" may be used interchangeably. One or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

In another embodiment, the agent is a nucleic acid based drug, such as DNA, RNA, modified DNA, modified RNA, antisense oligonucleotides, expression plasmid systems, nucleotides, modified nucleotides, nucleosides, modified nucleosides, nucleic acid ligands (e.g. aptamers), intact genes, a promotor complementary region, a repressor complementary region, an enhancer complementary region, and combinations thereof. A promotor complementary region, a repressor complementary region, an enhancer complementary region can be fully complementary or partially complementary to the DNA promotor region, repressor region, an enhancer region of a gene for which it is desirable to modulate expression.

In a preferred embodiment of the present invention, the agent to be delivered may be a mixture of agents. For example, a local anesthetic may be delivered in combination with an anti-inflammatory agent such as a steroid. Local anesthetics may also be administered with vasoactive agents such as epinephrine. To give another example, an antibiotic may be combined with an inhibitor of the enzyme commonly produced by bacteria to inactivate the antibiotic (e.g., penicillin and clavulanic acid).

In one embodiment, the controlled release polymer systems of the conjugates of the invention include a fluorescent molecule as a diagnostic agent.

Other diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

The controlled release polymer systems used in the conjugates of the invention may include radionuclides as either therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming the conjugate of the invention include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, and $^{18}$F.

In another embodiment, the controlled release polymer systems used in the conjugates of the invention may include a diagnostic or prognostic agent used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al., *Chemical Society Reviews* (1998), 27:19-29, the entire teachings of which are incorporated herein by reference.

Prophylactic agents that can be included in the conjugates of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

When conjugating nucleic acid ligands to controlled release polymer systems, it is desirable to have a polymer system which can be efficiently linked to the negatively charged nucleic acid ligands using simple chemistry without adversely affecting the 3-dimensional characteristic and conformation of the nucleic acid ligands, which is important for its target recognition. It is also desirable that a delivery vehicle should be able to avoid uptake by the mononuclear phagocytic system after systemic administration so that it is able to reach specific tissues and cells in the body. Polymers that are suitable for the controlled release polymer system include, but are not limited to, poly(lactic acid), poly(lactic-co-glycolic acid), polyanhydrides, poly(ortho esters)poly(caprolactone), polylysine, poly(ethylene imine), poly(acrylic acid), poly(urethane), and derivatives thereof. Preferred derivatives are polymers that have been PEGylated (i.e., covalently linked to polyethylene glycol), such as PEGylated poly(lactic acid), PEGylated poly(lactic-co-glycolic acid), PEGylated poly(caprolactone), PEGylated poly(ortho esters), PEGylated polylysine, and PEGylated poly(ethylene imine). In some instances, polymers that have a positive surface charge may result in a non-specific nucleic acid ligand-polymer interaction. This may result in decrease specific binding properties of some of the nucleic acid ligands bound to the controlled release polymer system. Therefore, in a preferred embodiment, the polymer carries a neutral to negative charge on its surface. Examples of polymer particles that carry a neutral to negative surface charge include, but are not limited to, polysebacic anhydride (PSA) and poly(lactic acid). These polymers may be modified to carry a more negative charge; an example being the addition of a terminal carboxylic acid group to poly (lactic acid).

Positively charged polymers such as poly(ethylene imine) or polylysine are typically used for nucleic acid encapsulation and gene delivery. However, as discussed above, positively charged polymers may interact with the negatively charged nucleic acid ligands and adversely affect their 3-dimensional characteristics and conformation and thereby disrupt target recognition of some of the nucleic acid ligands bound to the controlled release polymer system. One method of decreasing the charge interaction between the controlled release polymer system and nucleic acid ligand is to create a hydrophilic layer on the surface of the polymer particles by attaching polyethyleneglycol (PEG) to the surface of the polymer to shield the particles from interacting with nucleic acid ligands. In addition, many investigators have reported that the hydrophilic PEG group will increase plasma half-life by decreasing the uptake of the polymer by the phagocytic system while decreasing transfection/uptake efficiency by cells. Interestingly, lower transfection/uptake efficiency as a result of PEG placement on the surface of nanoparticles is a favorable factor for targeted delivery because it will potentially decrease non-specific transfection/uptake, while the presence of conjugated nucleic acid ligands on the polymer surface will increase transfection/uptake efficiency in targeted cells. Therefore, a dramatic decrease in transfection/uptake efficiency on cells which do not express the target of the nucleic acid ligand and a relatively less severe reduction in transfection/uptake efficiency in cells which do express these targets is expected.

The controlled release polymer system can be attached to the nucleic acid ligand directly or via a linker. When the nucleic acid ligand is attached directly to the controlled release polymer system, it is preferably attached by forming a covalent bond between a functional group on the nucleic acid ligand, such as an amine, a thiol or a hydroxy group, and a functional group on the controlled release polymer system, such as a carboxylic acid, an anhydride, a maleimide, an aldehyde group, etc. In a preferred embodiment, a linker is used to attach the controlled release polymer system to the nucleic acid ligand. A linker typically has a functional group that can form a bond with the nucleic acid ligand and a functional group that can form a bond with the controlled release polymer system. The functional groups of the linker can be separated by one or more atoms that are relatively non-reactive, such as an alkylene or a polyether (e.g., —{O(CH$_2$)$_m$}$_n$—). In one embodiment, either the bond between the linker and the nucleic acid ligand, or the bond between the linker and the controlled release polymer system, or both bonds are covalent. In addition, monomers are available for chemical synthesis of nucleic acids that have a linker attached to the nucleotide base or sugar (e.g., see www.trilinkbiotech-.com). These monomers can be incorporated into the nucleic acid ligand during chemical synthesis.

Typically, the number of functional groups on the surface of the nano- or microparticle will determine the aptamer surface density. In one embodiment, PEGylated PLA is modified to have surface maleimide groups which can react with aptamers containing thiol groups. In this embodiment, the nano- or microparticles are prepared from a mixture of PLA-PEG-MAL and PLA-PEG in which the ratio of PLA-PEG-MAL and PLA-PEG determines the density of maleimide groups on particle surface. The nanoparticles can have a ratio in the range of between about 0.01:10 and about 10:1 PLA-PEG-MAL to PLA-PEG. In one embodiment, the ratio of PLA-PEG-MAL to PLA-PEG is about 1:10.

Alternatively, the controlled release polymer system can be attached to the nucleic acid ligand directly or indirectly via a non-covalent interactions. Non-covalent interactions include but are not limited to the following:

1) Charge Interactions: For example, the controlled release polymer system may have a cationic surface or may be reacted with a cationic polymer, such as poly(lysine) or poly(ethylene imine), to provide a cationic surface. The polymer surface can then bind via charge interactions with a negatively charged nucleic acid ligand. One end of the nucleic acid ligand is, typically, attached to a negatively charged polymer (e.g., a poly(carboxylic acid)) or an additional oligonucleotide sequence that can interact with the cationic polymer surface without disrupting the binding affinity of the nucleic acid ligand for its target.

2) Affinity Interactions: For example, biotin may be attached to the surface of the controlled release polymer system and streptavidin may be attached to the nucleic acid ligand; or conversely, biotin may be attached to the nucleic acid ligand and the streptavidin may be attached to the surface of the controlled release polymer system. The biotin group and streptavidin are typically attached to the controlled release polymer system or to the nucleic acid ligand via a linker, such as an alkylene linker or a polyether linker. Biotin and streptavidin bind via affinity interactions, thereby binding the controlled release polymer system to the nucleic acid ligand.

3) Metal Coordination: For example, a polyhistidine may be attached to one end of the nucleic acid ligand, and a nitrilotriacetic acid can be attached to the surface of the controlled release polymer system. A metal, such as $Ni^{+2}$, will chelate the polyhistidine and the nitrilotriacetic acid, thereby binding the nucleic acid ligand to the controlled release polymer system.

4) Physical Adsorption: For example, a hydrophobic tail, such as polymethacrylate or an alkyl group having at least about 10 carbons, may be attached to one end of the nucleic acid ligand. The hydrophobic tail will adsorb onto the surface of a hydrophobic controlled release polymer system, such as a controlled release polymer system made of or coated with a polyorthoester, polysebacic anhydride, or polycaprolactone, thereby binding the nucleic acid ligand to the controlled release polymer system.

5) Host-Guest Interactions: For example, a macrocyclic host, such as cucurbituril or cyclodextrin, may be attached to the surface of the controlled release polymer system and a guest group, such as an alkyl group, a polyethylene glycol, or a diaminoalkyl group, may be attached to the nucleic acid ligand; or conversely, the host group may be attached to the nucleic acid ligand and the guest group may be attached to the surface of the controlled release polymer system. In one embodiment, the host and/or the guest molecule may be attached to the nucleic acid ligand or the controlled release polymer system via a linker, such as an alkylene linker or a polyether linker.

6) Hydrogen Bonding Interactions: For example, an oligonucleotide having a particular sequence may be attached to the surface of the controlled release polymer system, and an essentially complementary sequence may be attached to one or both ends of the nucleic acid ligand such that it does not disrupt the binding affinity of the nucleic acid ligand for its target. The nucleic acid ligand will then bind to the controlled release polymer system via complementary base pairing with the oligonucleotide attached to the controlled release polymer system. Two oligonucleotides are essentially complimentary if about 80% of the nucleic acid bases on one oligonucleotide form hydrogen bonds via an oligonucleotide base pairing system, such as Watson-Crick base pairing, reverse Watson-Crick base pairing, Hoogsten base pairing, etc., with a base on the second oligonucleotide. Typically, it is desirable for an oligonucleotide sequence attached to the controlled release polymer system to form at least about 6 complementary base pairs with a complementary oligonucleotide attached to the nucleic acid ligand.

Once the inventive conjugates have been prepared, they may be combined with pharmaceutical acceptable carriers to form a pharmaceutical composition. As would be appreciated by one of skill in this art, the carriers may be chosen based on the route of administration as described below, the location of the target issue, the drug being delivered, the time course of delivery of the drug, etc.

As used herein, the term "pharmaceutically acceptable carrier" means a non-toxic, inert solid, semi-solid or liquid filler, diluent, encapsulating material or formulation auxiliary of any type. *Remington's Pharmaceutical Sciences Ed.* by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be administered to a patient by any means known in the art including oral and parenteral routes. The term "patient", as used herein, refers to humans as well as non-humans, including, for example, mammals, birds, reptiles, amphibians, and fish. Preferably, the non-humans are mammals (e.g., a rodent, a mouse, a rat, a rabbit, a monkey, a dog, a cat, a primate, or a pig). In certain embodiments parenteral routes are preferred since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In a particularly preferred embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the inventive conjugate with suitable non-irritating excipients or carriers such as cocoa butter, polyethylene glycol, or a suppository wax which are solid at ambient temperature but liquid at body temperature and therefore melt in the rectum or vaginal cavity and release the inventive conjugate.

Dosage forms for topical or transdermal administration of an inventive pharmaceutical composition include ointments, pastes, creams, lotions, gels, powders, solutions, sprays, inhalants, or patches. The inventive conjugate is admixed under sterile conditions with a pharmaceutically acceptable carrier and any needed preservatives or buffers as may be required. Ophthalmic formulations, ear drops, and eye drops are also contemplated as being within the scope of this invention. The ointments, pastes, creams, and gels may contain, in addition to the inventive conjugates of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof. Transdermal patches have the added advantage of providing controlled delivery of a compound to the body. Such dosage forms can be made by dissolving or dispensing the inventive conjugates in a proper medium. Absorption enhancers can also be used to increase the flux of the compound across the skin. The rate can be controlled by either providing a rate controlling membrane or by dispersing the inventive conjugates in a polymer matrix or gel.

Powders and sprays can contain, in addition to the inventive conjugates of this invention, excipients such as lactose, talc, silicic acid, aluminum hydroxide, calcium silicates, and polyamide powder, or mixtures thereof. Sprays can additionally contain customary propellants such as chlorofluorohydrocarbons.

When administered orally, the inventive conjugates are preferably, but not necessarily, encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer *J. Control. Release* 5:13, 1987; Mathiowitz et al. *Reactive Polymers* 6:275, 1987; Mathiowitz et al. *J. Appl. Polymer Sci.* 35:755, 1988; Langer *Acc. Chem. Res.* 33:94, 2000; Langer *J. Control. Release* 62:7, 1999; Uhrich et al. *Chem. Rev.* 99:3181, 1999; Zhou et al. *J. Control. Release* 75:27, 2001; and Hanes et al. *Pharm. Biotechnol.* 6:389, 1995). Preferably the inventive conjugates are encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups, and elixirs. In addition to an encapsulated or unencapsulated conjugate, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents. As used herein, the term "adjuvant" refers to any compound which is a nonspecific modulator of the immune response. In certain preferred embodiments, the adjuvant stimulates the immune response. Any adjuvant may be used in accordance with the present invention. A large number of adjuvant compounds is known in the art (Allison *Dev. Biol. Stand.* 92:3-11, 1998; Unkeless et al. *Annu. Rev. Immunol.* 6:251-281, 1998; and Phillips et al. *Vaccine* 10:151-158, 1992).

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

It will be appreciated that the exact dosage of the inventive conjugate is chosen by the individual physician in view of the patient to be treated. In general, dosage and administration are adjusted to provide an effective amount of the inventive conjugate to the patient being treated. As used herein, the "effective amount" of an inventive conjugate refers to the amount necessary to elicit the desired biological response. As will be appreciated by those of ordinary skill in this art, the effective amount of inventive conjugate may vary depending on such factors as the desired biological endpoint, the drug to be delivered, the target tissue, the route of administration, etc. For example, the effective amount of inventive conjugate containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The conjugates of the invention are preferably formulated in dosage unit form for ease of administration and uniformity of dosage. The expression "dosage unit form" as used herein refers to a physically discrete unit of conjugate appropriate for the patient to be treated. It will be understood, however, that the total daily usage of the compositions of the present invention will be decided by the attending physician within the scope of sound medical judgment. For any conjugate, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of conjugates can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use.

These and other aspects of the present invention will be further appreciated upon consideration of the following Examples, which are intended to illustrate certain particular embodiments of the invention but are not intended to limit its scope, as defined by the claims.

EXAMPLES

Example 1

Preparation of Polymers

A. Materials

Poly(lactic acid) (PLA), poly(lactic-co-glycolic acid) (PLGA), and PLA-COOH were purchased from a commercial vendor. Polyanhydrides, poly(caprolactone), pegylated PLA or PLGA (PLA-PEG-maleimide, PLGA-PEG-maleimide, PLA-PEG-COOH, and PLGA-PEG-COOH), and copolymers of poly(acrylic acids) derivatives were synthesized according to known literature methods. Polymeric cations such as poly(L-lysine) (PLL) and poly(ethylene imines) (PEI) were purchased from commercial vendors. Some chemicals such as N-hydroxysuccinimide (NHS), 1-[3-(dimethylamino)propyl]-3-ethylcarbodiimide hydrochloride (EDC), tin(II) 2-ethylhexanoate, $_{D,L}$-Lactide, monomethylpoly(ethyleneglycol) (mPEG, average Mn ca. 2000), toluene (99.8%, anhydrous) were purchased from Aldrich Chemical Co (Milwaukee, Wis., USA). Maleimide-PEG$_{3500}$-OH and COOH-PEG$_{3500}$-OH were custom synthesized by Nektar Therapeutics. Nucleic acid ligand A10 which binds to prostate specific membrane antigen (PSMA) was prepared as described in Lupold, S. E., et al., *Cancer Research* (2002), 62:4029-4033, the entire teachings of which are incorporated herein by reference. At the 3'-end, the nucleic acid ligand has a 5'-deoxythymine that is linked to the nucleic acid ligand by a 3'-3' linkage. In addition, the 5'-end of the nucleic acid ligand has an 18 carbon linker that terminates in a thiol group (hereinafter "thiol-18C-aptamer") or an 18 carbon linker that terminates in an amine (hereinafter "amine-18C-aptamer").

B. PEGylated PLA Polymers:

Maleimide-poly(ethyleneglycol)-block-poly($_{D,L}$-lactic acid) (PLA-PEG-MAL), COOH-poly(ethyleneglycol)-block-poly($_{D,L}$-lactic acid) (PLA-PEG-COOH), and methoxypoly(ethyleneglycol)-block-poly($_{D,L}$-lactic acid) (PLA-mPEG) were synthesized by ring opening polymerization in anhydrous toluene using tin (II) 2-ethylhexanoate as catalyst. General procedure for syntheses of the copolymers is as follows. $_{D,L}$-Lactide (1.6 g, 11.1 mmol) and MAL-PEG$_{3500}$-OH (0.085 mmol) or COOH-PEG$_{3500}$-OH (0.085 mmol) in anhydrous toluene (10 mL) was heated to reflux temperature (ca. 120° C.), after which the polymerization was initiated by adding tin (II) 2-ethylhexanoate (20 mg). After stirring for 9 h with reflux, the reaction mixture was cooled to room temperature. To this solution was added cold water (10 mL) and then resulting suspension was stirred vigorously at room temperature for 30 min to hydrolyze unreacted lactide monomers. The resulting mixture was transferred to separate funnel containing CHCl$_3$ (50 mL) and water (30 mL). After layer separation, organic layer was collected, dried using anhydrous MgSO$_4$, filtered, and concentrated under reduced vacuum. Then, hexane was added to the concentrated solution to precipitate polymer product. Pure PLA-PEG$_{3500}$-MAL or PLA-PEG$_{3500}$-COOH was collected as a white solid. PLA-mPEG$_{2000}$ was also prepared by same procedure above. Both copolymers were characterized by $^1$H-NMR (400 MHz, Bruker Advance DPX 400) and gel permeation chromatography (GPC) (Waters Co, Milford, Mass., USA).

C. Polyanhydrides, Poly(Sebacic Acids):

Sebacic aicds (50 g) are reacted with excess of acetic anhydride (500 mL) in a fractional distillation setup. The distillation rate is adjusted to 100 mL/h. The reflux lasted between 1 and 2 h, with occasional replenishment of fresh acetic anhydride. The rest of solvent was evaporated in a rotary evaporator at 70° C., and the residue was recrystallized in a mixture solvent of chloroform and petroleum ether (20:80 v/v). The condensation of the prepolymer is then carried out in an evaporator under $10^{-4}$ mmHg at 120° C. for 12-36 h. The polymer was purified by reprecipitation in petroleum ether.

Example 2

Preparation of Nano- and Microparticles

A. Preparation of Drug-Encapsulated Nano- or Microparticles

A water-in-oil-in-water (W/O/W) solvent evaporation procedure will be used to generate drug-encapsulated nanoparticles. Polymer (example: PLA, PLA-PEG, PLA-COOH, PLA-PEG-COOH, PLA-MAL, PLA-PEG-MAL, poly(sebacic anhydride), etc.) is dissolved in dichloromethane (at 2-10%); an aqueous solution of certain drug will then be added to polymer solution at 4-20% v/v. In model studies, rhodamine or rhodamine-conjugated dextran (at 10 μg/μL) was used as a model small and large molecule drugs, respectively. (For lypophilic drugs, the drug and polymer are mixed together in the dichloromethane, and the procedure then becomes an oil-in-water solvent evaporation process.) The aqueous drug and organic polymer phases are then emulsified using probe sonicator (10 W for 10-90 s). This emulsion is then added to poly(vinyl alcohol) solution (0.1-5% final concentration) or sodium cholate solution (0.1-5% final concentration). A second emulsion can be prepared by sonication (18 W for 10-90 s) to make nanoparticles or by mechanical stirring at 3000-10000 rpm to make microparticles. The organic solvent is evaporated from the W/O/W emulsion using rotary evaporator. The nano- or microparticles formed are then washed three times by suspending the particles in deionized and distilled water followed by centrifugation.

B. Preparation of Drug-Encapsulated Nano- or Microparticles with Different Densities of Aptamers on the Surface.

PEGylated poly(lactic acid) with maleimide functional group (PLA-PEG-MAL) nanoparticles were prepared using double emulsion solvent evaporation method. Poly (lactic acid)-poly (ethylene glycol)-Maleimide en-block copolymer ($PLA_{10800}$-$PEG_{3500}$-MAL and poly (lactic acid)-poly (ethylene glycol)-methoxy en-block copolymer ($PLA_{11300}$-$mPEG_{2000}$) were synthesized by ring opening polymerization in anhydrous toluene using stannous octoate as a catalyst. An aqueous solution of rhodamine or rhodamine-conjugated dextran (10 μg/μl) was emulsified in dichloromethane dissolving both copolymers with a probe sonicator. The optimal ratio of $PLA_{10800}$-$PEG_{3500}$-MAL to $PLA_{11300}$-$mPEG_{3500}$ determines the density of maleimide, and the aptamers, on the surface of nanoparticles since thiol—modified aptamers will be conjugated to MAL groups. The nanoparticles were prepared with a ratio of 1:10 of PLA-PEG-MAL to PLA-mPEG, a ratio derived by estimation given the predicted size of the aptamer. The resulting emulsion was stirred at room temperature to evaporate the dichloromethane and the resulting nanoparticles were centrifuged, collected and resuspended in distilled water.

C. Preparation of the Gene-Containing Nanoparticles

Gene-contained nanoparticles were formed by adding polyethyleneimine (PEI) or poly(L-lysine) (PLL) solution in 25 mM of HEPES buffer, pH 7.0 (concentrations adjusted to yield desired DNA/polymer weight ratios) to a plasmid DNA solution (pCMV-Luc as a model gene; 0.1 μg/μL in water) in a tube. The resulting mixtures were gently vortex and allowed to stand at room temperature for 15 min.

D. Characterization of Nano- and Microparticles

Particles were characterized for their sizes, surface charge and surface morphology using Quasi-elastic laser light scattering (QELS), ZetaPALS dynamic light scattering detector, and scanning electron microscopy (SEM), respectively. The nanoparticles generated from PLA, PLA-PEG-MAL, PLA-COOH, and PLA-PEG-COOH were monodispersed with an average size of 252 nm±11 nm, 137 nm±15 nm, 265 nm±10 nm and 241 nm±26 nm (mean SD, n=3), respectively (summarized in Table 1). The 1-potential of the PLA-COOH and PLA-PEG-COOH nanoparticles however was significantly more negative than the unmodified PLA particle as predicted (−95 mV±6 mV for PLA-COOH and −50 mV±3 mV for PLA-PEG-COOH vs. −24 mV±5 mV for PLA, mean±SD, n=3). The PLA, PLA-COOH and PLA-PEG-COOH microparticles were 2420 nm±270 nm, 1972 nm±459 nm, 2805 nm±301 nm, in size, with a ζ-potential of −23 mV±9 mV, −87 mV±17 mV and −51 mV±2 mV, respectively (mean±SD, n=3). The surface morphology and size distribution of particles from all four polymer systems were determined by SEM, and representative images of PLA-COOH and PLA-PEG-COOH nanoparticles and microparticles are shown (FIG. 1).

TABLE 1

Using PLA, PLA-PEG-MAL, PLA-COOH and PLA-PEG-COOH polymer systems, nanoparticles and microparticles were generated by double emulsion method (described above). Particles were characterized for particle size (nm) and zeta-potential (mV). Data represents mean ± SD, n = 3.

| Particles | Mean Particle Size (nm) | Zeta Potential (mV) |
|---|---|---|
| PLA | 252 ± 11 | −24 ± 5 |
| PLA | 2420 ± 270 | −23 ± 9 |
| PLA-PEG-MAL | 137 ± 15 | −17 ± 2 |
| PLA-COOH | 265 ± 10 | −95 ± 6 |
| PLA-COOH | 1972 ± 459 | −87 ± 17 |
| PLA-PEG-COOH | 241 ± 26 | −50 ± 3 |
| PLA-PEG-COOH | 2805 ± 301 | −51 ± 2 |

Example 3

Nucleic Acid Ligand-Polymer Particle Conjugates

A. Preparation of a Nucleic Acid Ligand Conjugated to MAL-PEG-PLA or PLA-MAL particles Thiol modified aptamers (thiol-18C-aptamer) (1 nmol) will be dissolved in 100 ml of PBS and incubated in the presence of 30 ml of TCEP at room temperature for 30 min. Equimolar ratio (with regards to maleimide groups) of polymer particles dispersed in distilled water were added to the aptamer and the incubation will continue for 10 h under gentle agitation. The resulting solution was dialyzed with DispoDialyzer, MWCO 300,000 (Spectrum Laboratories, Inc., CA) for 2 h in 200 ml distilled water, with 1 change to dialysis solution at 30 min. The aptamer conjugated particles were collected by centrifugation as previously described.

Figure 2:
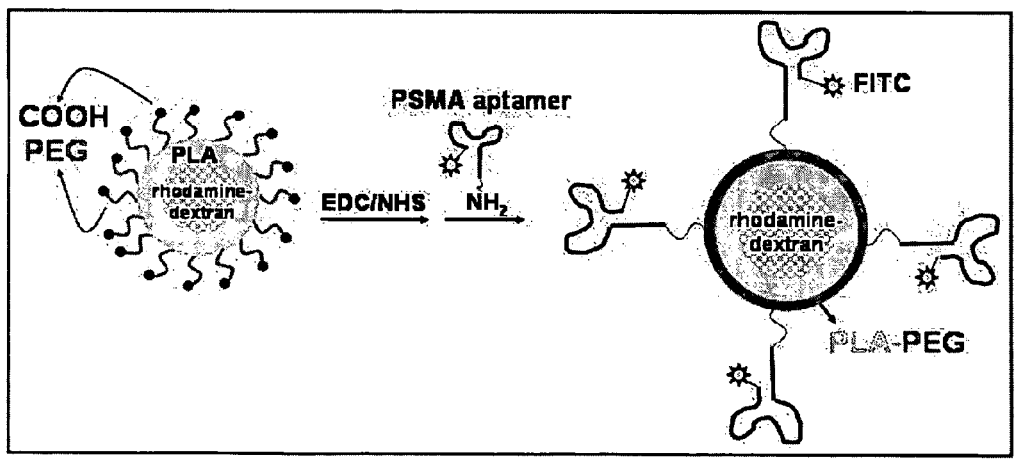
FIG. 2 is a schematic representation of a conjugation strategy for covalently attaching 3'-amine-modified aptamers to PLA-PEG-COOH particles encapsulating rhodamine-dextran (as a model drug).

B. Preparation of a Nucleic Acid Ligand Conjugated to PLA-COOH and PLA-PEG-COOH particles Approximately 1 mg of PLA-COOH or PLA-PEG-COOH particles were incubated with 1 ml of 400 mM EDC and 100 mM NHS for 30 min. at room temperature with constant stirring. Particles were washed 3 times with distilled water and collected by centrifugation. Particles were resuspended in PBS and 1 nmol of amine-modified aptamers (amine-18C-aptamer) was added to the activated particles and the mixture was gently mixed for several hours at room temperature. The resulting aptamer-nanoparticle conjugates or aptamer-microparticle conjugates were purified by dialysis using DispoDialyzer, MWCO 100,000 (Spectrum Laboratories, Inc., CA) for 2 h in 200 ml distilled water. A schematic representation of this synthesis can be seen in FIG. 2.

C. Preparation of a Nucleic Acid Ligand Conjugated to Poly(sebacic anhydride) Particles The anhydride bond that links the polymer's monomeric units readily reacts with free amine groups under basic conditions. Nanoparticles and amine-18C linker-aptamer were mixed at 10:1 molar ratios in 0.2 M borate buffer (pH 9) at room temperature for 10 min under gentle agitation. The resulting nanoparticle-aptamer conjugates were washed 3 times with distilled water and collected by centrifugation and characterized as described below.

D. Preparation of a Nucleic Acid Ligand conjugated to $O_2$ Plasma-Treated PLA Particles PLA particles are exposed to oxygen-plasma for 5-30 min. which causes the generation of carboxylic acid groups over the surface of the particles. 1-(3-Dimethylaminopropyl)-3-ethylcarbodiimide hydrochloride (EDC) (1 mL, 400 mM in distilled water) and N-hydroxysuccinimide (NHS) (1 mL, 100 mM in distilled water) are added to 10 mg of carboxylic acid surface modified PLA particles. A nucleic acid ligand having a linker that has a free primary or secondary amine group is then added and incubated for several hours at room temperature. The nucleic acid ligand-PLA particle conjugates are washed by suspending the conjugates in deionized distilled water and centrifuged three times.

E. Evaluation and Characterization of the Polymeric Particles and Bioconjugates

Figure 3:
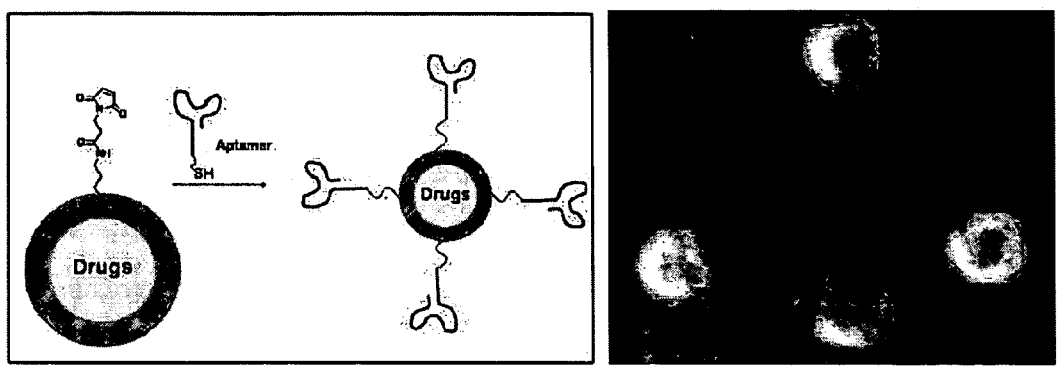
FIG. 3 is a scanning electron micrograph of nanoparticle-aptamer bioconjugates generated by incubating 3'-thiol modified aptamers with nanoparticles generated from poly (ethylene glycol)-poly (lactic acid) en-block co-polymer with a terminal malimide group (PLA-PEG-MAL)
Figure 3:
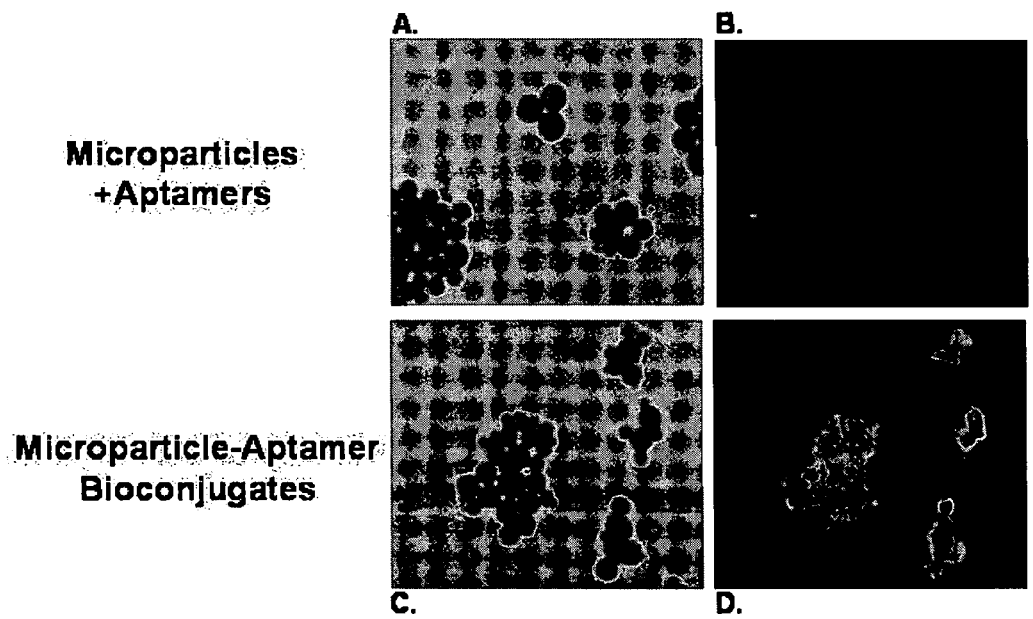

The polymeric particles before and after nucleic acid ligand conjugation were characterized using several standard analytical means. The size of the particles and ζ-potentials (surface potential) were measured by Quasi-elastic laser light scattering (QELS) using a ZetaPALS dynamic light scattering detector (Brookhaven Instruments Corporation, 15 mW laser, incident beam=676 nm). Surface morphology and size were characterized by scanning electron microscopy and transmission electron microscopy (instruments provided through MIT shared facilities). A scanning electron micrograph of the rhodamine-dextran nanoparticle-nucleic acid ligand conjugate is shown in FIG. 3. The surface of the polymeric particles were analyzed using X-ray photoelectron spectroscopy (XPS).

In addition, to assess the extent of conjugation of A10 aptamer to PLA-PEG-COOH nano- and microparticles, A10 aptamers were 5'-FITC-labeled and 3'-amine modified so that conjugation of the aptamers to nano- or microparticles would yield fluorescent bioconjugates. The acid group on the particle surface was first converted to NHS ester in the presence of EDC, and the covalent coupling reaction between the amine modified aptamers and the particles were carried out as described above. By using different molar ratio of aptamers relative to the carboxylic acid groups in the reaction, particles with increasing amount of aptamers on particle surface were generated (data not shown). To assess the specificity of aptamer interaction with the particle surface, aptamers were incubated with microparticles either with or without the conversion of carboxylic acid to NHS ester (i.e. absence of EDC); thus, when the carboxylic acid was not converted to an NHS ester, any interaction between the fluorescent aptamer and the microparticles would be non-specific (e.g., charge interaction). FIG. 4A is a transmission light microscopy image of microparticles incubated with a 5'-FITC labeled, amine-modified aptamer in the absence of EDC (i.e., the COOH surface groups of the microparticle were not converted to an NHS ester and, therefore, could not react with the amine group of the aptamer). FIG. 4B is a fluorescent image of the microparticles in FIG. 4A showing that no detectable fluorescence is specifically associated with the microparticles indicating that there was no non-specific binding of the aptamer to the microparticles. In contrast, FIG. 4C shows a light microscope image of microparticles incubated with a 5'-FITC labeled, amine-modified aptamer in the presence of EDC. The fluorescent image of these microparticles, shown in FIG. 4D, indicates that the aptamer conjugates specifically to the microparticle.

Figure 4E:
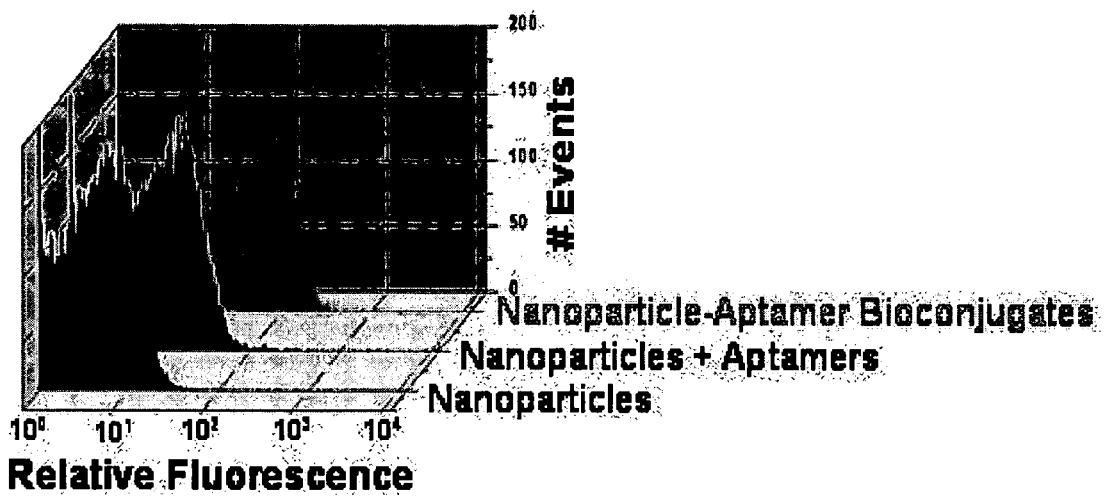
FIG. 4E is a graph indicating the increase in fluorescent intensity of nanoparticles (shown in black) after incubation with 5'-FITC labeled 3'-amine-modified aptamers in the absence of EDC (shown in blue) or after conjugation with a 5'-FITC labeled amine-modified aptamers in the presence of EDC (shown in green).

FIG. 4E is a graph comparing the relative fluorescence of nanoparticle alone (black); nanoparticles incubated with 5'-FITC-labeled, amine-modified aptamer in the absence of EDC (blue); and nanoparticles incubated with 5'-FITC-labeled, amine-modified aptamer in the presence of EDC (green). The bioconjugates resulting from the covalent linkage of aptamers and nanoparticles (green) demonstrated an approximate 7 fold increase in fluorescence when compared to nanoparticles that were incubated but had no covalent linkage to aptamers (blue). Thus, these experiments demonstrate that the conjugation reaction results in specific linkage between the aptamer and the particles in both nanoparticle-aptamer and microparticle-aptamer bioconjugates and that there is minimal non-specific charge interaction between aptamers and particles.

Example 4

Cellular Binding and Uptake of Nanoparticle-Aptamer Bioconjugates.

A. Specificity of Nanoparticle-Aptamer Bioconjugates

LNCaP cells (FIG. 5) and PC3 cells (FIG. 6) were grown on chamber slides and incubated in culture medium supplemented with rhodamine-dextran encapsulated PLA-PEG-COOH nanoparticles (50 μg) or rhodamine-dextran encapsulated PLA-PEG-COOH nanoparticles-aptamer bioconjugates (50 μg) (as prepared in Example 3B) for 2 hrs or 16 hrs. Cells were washed in PBS×3, fixed and permeabilized, stained with DAPI (nuclei) and Alexa-Flour Phalloidin (cytoskeleton), washed and analyzed by light transmission and fluorescent microscopy. The rhodamine-dextran encapsulated nanoparticles or nanoparticle-aptamer bioconjugates are shown in red under fluorescent microscopy.

Figure 5:
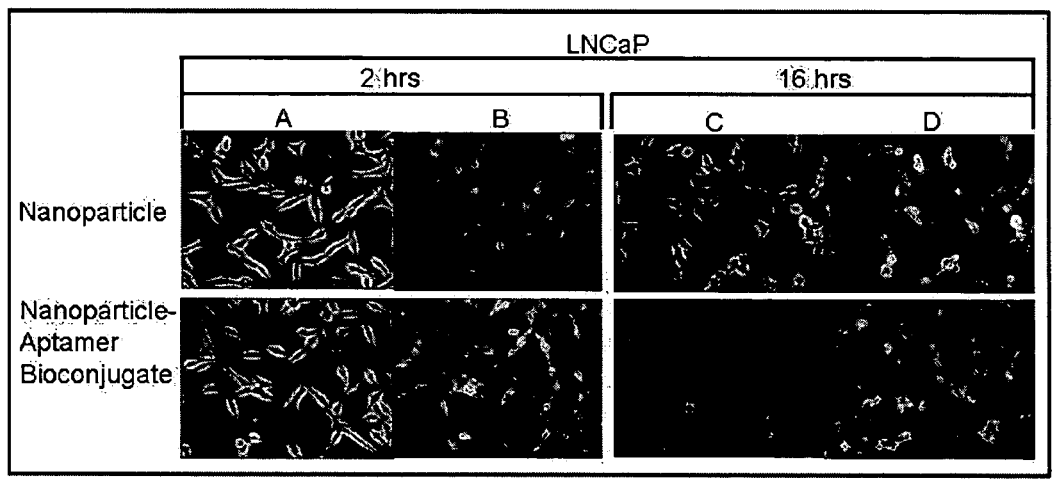
FIG. 5A is a light microscopy image of LNCaP cells incubated with rhodamine-dextran nanoparticles for 2 hrs (top panel) or with rhodamine-dextran nanoparticle-A10 aptamer bioconjugates for 2 hrs (bottom panel).
FIG. 5B is a fluorescent image of the LNCaP cells in FIG. 5A.
FIG. 5C is a light microscopy image of LNCaP cells incubated with rhodamine-dextran nanoparticles for 16 hrs (top panel) or with rhodamine-dextran nanoparticle-A10 aptamer bioconjugates for 16 hrs (bottom panel).
FIG. 5D is a fluorescent image of the LNCaP cells in FIG. 5C.
Figure 6:
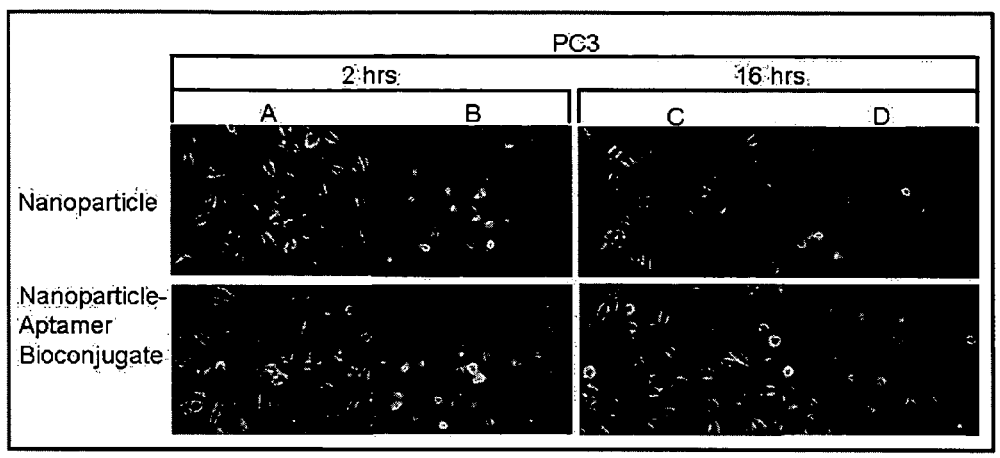
FIG. 6A is a light microscopy image of PC3 cells incubated with rhodamine-dextran nanoparticles for 2 hrs (top panel) or with rhodamine-dextran nanoparticle-A10 aptamer bioconjugates for 2 hrs (bottom panel).
FIG. 6B is a fluorescent image of the PC3 cells in FIG. 6A.
FIG. 6C is a light microscopy image of PC3 cells incubated with rhodamine-dextran nanoparticles for 16 hrs (top panel) or with rhodamine-dextran nanoparticle-A10 aptamer bioconjugates for 16 hrs (bottom panel).
FIG. 6D is a fluorescent image of the PC3 cells in FIG. 6C.

This time-course study demonstrates that the uptake of PEGylated nanoparticle-aptamer bioconjugates into LNCaP cells is significantly enhanced when compared to control PEGylated nanoparticles lacking the A10 aptamer (FIG. 5). In the case of PC3 prostate epithelial cells which do not express the PSMA protein, there was no measurable difference in particle uptake in the bioconjugate or the control nanoparticle group (FIG. 6). This data demonstrates that the increase in uptake efficiency of bioconjugates by LNCaP cells is clearly detectable at our earliest time-point of 2 hrs. By 16 hrs, the differential uptake of PEGylated nanoparticle-aptamer bioconjugates vs. control group becomes markedly pronounced. Furthermore, non-targeted PC3 cells show relatively low uptake efficiency of PEGylated nanoparticle-aptamer bioconjugates in even at 16 hrs. Several previous reports had demonstrated that PEGylated particles have a significantly lower uptake efficiency (or transfection efficiency in the case of gene delivery) as compared to equivalent non-PEGylated particles. This data demonstrates that the lower uptake efficiency is a favorable characteristic for the targeted delivery application of the invention and results in decreased non-specific uptake in non-targeted PC3 cells. While conjugation of aptamers to the surface of PEGylated particles overcomes this decrease in uptake efficiency, and results in delivery vehicles which are taken up specifically and efficiently by the targeted LNCaP cells (FIG. 5).

B. Internalization of Nanoparticle-Aptamer Bioconjugate

Figure 7:
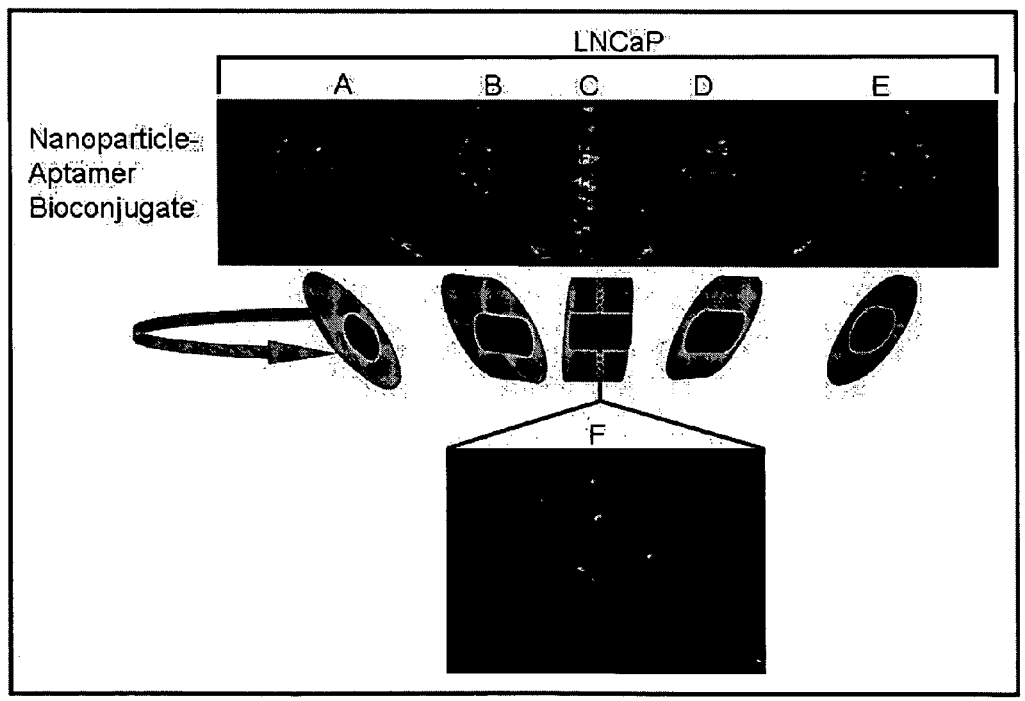
FIG. 7 is fluorescent images taken along the z-axis of a single LNCaP cell at 0.1 micrometer interval after incubation with rhodamine-dextran nanoparticle-A10 aptamer bioconjugate for 2 hrs. More than 200 images were taken at different cross-section depths and combined to generate a 3-dimensional structure of the cell. Panels A-E are representative images at different depths of the same LNCaP cell rotated at 45° intervals. Panel F represents a single image through the mid Z-axis point of the cell to demonstrate the uptake and intracellular localization of the nanoparticle-A10 aptamer bioconjugate.

LNCaP cells were grown on chamber slides and incubated in culture medium supplemented with rhodamine-dextran encapsulated nanoparticle-aptamer bioconjugates (50 μg) for 2 hrs, washed and analyzed at 100× magnification along their z-axis at 0.1 μm intervals by fluorescent microscopy. Images were combined to reconstruct a 3D image of the cell. FIG. 7, panels A through E represent the same LNCaP cell being rotated at 45 degree intervals. This rotation is schematically represented below each panel to show the position of cell and the axis of rotation. FIG. 7, panel F represents a single image through mid z-axis point of cell demonstrating particles at that depth and confirming the intracellular position of particles. The cell nuclei and the actin cytoskeleton are stained with blue (DAPI), and green (Alexa-Flour Phalloidin), respectively, in the fluorescent image. The intracellular rhodamine-dextran encapsulated nanoparticle-aptamer bioconjugates are shown in red in the fluorescent image. This data demonstrates that even at 2 hrs, the nanoparticles were largely internalized into cells. These data are reproducible with different batches of cells and nanoparticle-aptamer bioconjugate preparations.

What is claimed is:

1. A controlled release polymer nanoparticle, comprising;
   a therapeutic or diagnostic agent incorporated in the controlled release polymer nanoparticle; and
   a nucleic acid ligand comprising an oligonucleotide bound to the surface of the controlled release polymer nanoparticle that selectively binds to a target cell or tissue, and thereby delivers the controlled release polymer nanoparticle to the target cell or tissue;
   wherein the controlled release polymer nanoparticle carries a neutral to negative charge on its surface; and
   wherein the bound oligonucleotide has a folded three-dimensional conformation resulting from intramolecular interactions.

2. The controlled release polymer nanoparticle of claim 1, wherein the nucleic acid ligand is prepared using L-enantiomeric nucleosides.

3. The controlled release polymer nanoparticle of claim 1, wherein one or more internal nucleotides at the 3'-end, 5'-end, or both at the 3'- and 5'-end of the nucleic acid ligand are inverted to yield a 3'-3' or a 5'-5' nucleotide linkage.

4. The controlled release polymer nanoparticle of claim 1, wherein one or more of the nucleotides of the nucleic acid ligand are bound to another nucleotide by a hydrocarbon linker or a polyether linker.

5. The controlled release polymer nanoparticle of claim 1, wherein the nucleic acid ligand binds to a protein, a carbohydrate, a lipid or a nucleic acid.

6. The controlled release polymer nanoparticle of claim 5, wherein the nucleic acid ligand binds to a protein selected from the group consisting of tumor-markers, integrins, cell surface receptors, transmembrane proteins, ion channels, membrane transport protein, enzymes, antibodies, and chimeric proteins.

7. The controlled release polymer nanoparticle of claim 5, wherein the nucleic acid ligand binds to a nucleic acid selected from the group consisting of DNA, RNA, modified DNA, modified RNA, and combinations thereof.

8. The controlled release polymer nanoparticle of claim 1, further comprising an agent for localization.

9. The controlled release polymer nanoparticle of claim 8, wherein the localizing agent is a magnetic particle.

10. The controlled release polymer nanoparticle of claim 1, wherein the controlled release polymer nanoparticle releases a therapeutic agent.

11. The controlled release polymer nanoparticle of claim 10, wherein the therapeutic agent is selected from the group consisting of small molecule drugs, protein drugs, radionuclides, nucleic acid based drugs, and combinations thereof.

12. The controlled release polymer nanoparticle of claim 11, wherein the therapeutic agent is a small molecule drug selected from the group consisting of an antibiotic, an antiviral agent, an antiparasitic agent, an anti-cancer agent, a radionuclide, an anticoagulant, an analgesic agent, an anesthetic agent, an ion channel potentiator, and ion channel inhibitor, an anti-inflammatory agent, and combinations thereof.

13. The controlled release polymer nanoparticle of claim 11, wherein the therapeutic agent is a nucleic acid based drug selected from the group consisting of DNA, RNA, modified DNA, modified RNA, antisense oligonucleotides, expression plasmid systems, intact genes, intact or partially complementary DNA promoter regions of gene expression, intact or partially complementary DNA repressor regions of gene expression, intact or partially complementary DNA enhancer regions of gene expression, nucleotides, modified nucleotides, nucleosides, modified nucleosides, nucleic acid ligands, and combinations thereof.

14. The controlled release polymer nanoparticle of claim 1, wherein the diagnostic agent is an iron oxide particle.

15. The controlled release polymer nanoparticle of claim 1, wherein the diagnostic agent is a gadolinium complex.

16. The controlled release polymer nanoparticle of claim 1, wherein the controlled release nanoparticle releases a prophylactic agent.

17. The controlled release polymer nanoparticle of claim 1, wherein the controlled release polymer nanoparticle comprises poly(lactic acid).

18. The controlled release polymer nanoparticle of claim 1, wherein the controlled release polymer nanoparticle comprises poly(lactic acid) with a terminal carboxylic acid group or a terminal maleimide group.

19. The controlled release polymer nanoparticle of claim 1, wherein the controlled release polymer nanoparticle comprises PEG-poly(lactic acid) co-polymer.

20. The controlled release polymer nanoparticle of claim 1, wherein the controlled release polymer nanoparticle comprises poly(lactic-co-glycolic acid).

21. The controlled release polymer nanoparticle of claim 1, wherein the controlled release polymer nanoparticle comprises poly(lactic-co-glycolic acid) with a terminal carboxylic acid group or a terminal maleimide group.

22. The controlled release polymer nanoparticle of claim 1, wherein the controlled release polymer nanoparticle comprises PEG-poly(lactic-co-glycolic acid) co-polymer.

23. The controlled release polymer nanoparticle of claim 1, wherein the controlled release polymer nanoparticle comprises poly(glycolic acid).

24. The controlled release polymer nanoparticle of claim 1, wherein the controlled release polymer nanoparticle comprises PEG-poly(glycolic acid) co-polymer.

25. The controlled release polymer nanoparticle of claim 1, wherein the controlled release polymer nanoparticle comprises poly(caprolactone).

26. The controlled release polymer nanoparticle of claim 1, wherein the controlled release polymer nanoparticle comprises a polyanhydride.

27. The controlled release polymer nanoparticle of claim 1, wherein the controlled release polymer nanoparticle is attached to the nucleic acid ligand by a linker.

28. The controlled release polymer nanoparticle of claim 27, wherein the linker comprises an alkylene chain, a hydrocarbon chain, or a polyether chain.

29. The controlled release polymer nanoparticle of claim 1, wherein the controlled release polymer nanoparticle comprises poly(lactic acid)-PEG- maleimide and poly(lactic acid)-PEG.

30. The controlled release polymer nanoparticle of claim 1, wherein the controlled release polymer nanoparticle has a zeta potential ranging between −17 and −100 mV.

31. The controlled release polymer nanoparticle of claim 1, wherein the nucleic acid ligand is a spiegelmer.

32. The controlled release polymer nanoparticle of claim 1, wherein the controlled release polymer nanoparticle comprises a polymer that is biologically degradable, chemically degradable, or both biologically and chemically degradable.

33. The controlled release polymer nanoparticle of claim 32, wherein the controlled release polymer nanoparticle comprises a polymer selected from the group consisting of poly(lactic acid), derivatives of poly(lactic acid), PEGylated poly(lactic acid), poly(lactic-co-glycolic acid), derivatives of poly(lactic-co-glycolic acid), PEGylated poly(lactic-co-glycolic acid), a polyanhydride, poly(ortho esters), derivaties of poly(ortho esters), PEGylated poly(ortho esters), poly(caprolactone), derivatives of poly(caprolactone), PEGylated poly(caprolactone), poly(acrylic acid), derivatives of poly(acrylic acid), poly(urethane), derivatives of poly(urethane), and combinations thereof.

34. A composition comprising the controlled release polymer nanoparticle of claim 1 and a lipid.

35. A pharmaceutical composition, comprising a pharmaceutically acceptable carrier and a controlled release polymer nanoparticle of claim 1.

36. A method of delivering an agent to a target cell, comprising contacting a target cell or tissue with the controlled release polymer nanoparticle of claim 1.

37. A method of treating a patient with cancer, comprising administering to the patient a controlled release polymer nanoparticle system of claim 1.

* * * * *